United States Patent

Venturello et al.

[11] Patent Number: 5,520,844
[45] Date of Patent: * May 28, 1996

[54] IMIDE-AROMATIC PEROXYACIDS AS BLEACHING AGENTS

[75] Inventors: Carlo Venturello, Novara; Claudio Cavallotti; Fulvio Burzio, both of Milan, all of Italy

[73] Assignee: Ausimont S.p.A., Italy

[*] Notice: The portion of the term of this patent subsequent to Oct. 20, 2009, has been disclaimed.

[21] Appl. No.: 637,479

[22] Filed: Jan. 4, 1991

Related U.S. Application Data

[63] Continuation of Ser. No. 298,918, Jan. 19, 1989, abandoned.

[30] Foreign Application Priority Data

Jan. 20, 1988 [IT] Italy .................................. 19131 A/88

[51] Int. Cl.[6] .................................. C01B 15/10
[52] U.S. Cl. .................................. 252/186.42; 252/186.26; 252/95; 548/451; 548/477; 548/479
[58] Field of Search .................................. 548/451, 477, 548/479; 252/186.42, 186.26

[56] References Cited

U.S. PATENT DOCUMENTS 4,681,592  7/1987  Hardy et al. .................................. 8/111
5,061,807  10/1991  Gethoffer et al. .

FOREIGN PATENT DOCUMENTS 349940  7/1989  European Pat. Off. .
3823172  1/1990  Germany .
90/07501  7/1990  WIPO .

OTHER PUBLICATIONS

K. Balenovic et al. Chem. Abstracts, vol. 56, No. 4663F (1961).
K. Balenovic et al., J. Chem. Soc. (1962), pp. 3821–3822, "Preparation of Some Peroxy–Acids derived from Optically active Amino–Acids".

*Primary Examiner*—Philip Tucker
*Assistant Examiner*—Joseph D. Anthony
*Attorney, Agent, or Firm*—Bryan Cave

[57] ABSTRACT

Bleaching agents constituted by at least one imidearomatic (poly)peroxyacid, having the formula (I):

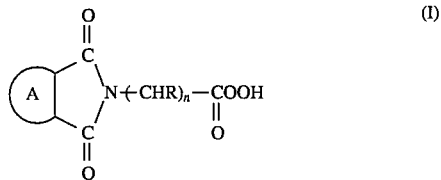

wherein A represents a residue of a substituted or unsubstituted benzene or naphthalene ring, R is a hydrogen atom, a lower alkyl group, an OH group, a COOH group, a COOOH group or a COOR' group wherein R' represents a $C_1$–$C_5$ alkyl group, and n is an integer from 1 to 5.

5 Claims, No Drawings

IMIDE-AROMATIC PEROXYACIDS AS BLEACHING AGENTS

This is a continuation of application U.S. Ser. No. 07/298,918 filed Jan. 19, 1989 now abandoned.

DISCLOSURE OF THE INVENTION

The present invention relates to peroxidic agents having a bleaching action.

More particularly, the present invention relates to bleaching agents based on imide-aromatic (poly)peroxycarboxylic acids, especially suitable for use in the washing of fabrics at low temperature.

The use of peroxygenated bleaching agents is known for the washing of fabrics, such as the inorganic peroxides (sodium perborate), which are efficacious only at a temperature above approximately 70° C. and which therefore are not suitable for use at lower operating conditions.

A class of products which develops a bleaching action at low temperature is constituted by the organic peroxides. Therefore, in recent years the organic peroxyacids have aroused an increasing interest in the industrial field, especially due to energy-saving considerations.

Therefore, a large number of literature references exists concerning the very considerable research activity aiming to find organic peroxyacid compounds endowed with the necessary requisites of bleaching activity, and, in particular, of thermal stability, these later requisites being essential for the purposes of an industrial and widespread application of such compounds.

Many either mono- or di-peroxycarboxylic, straight or cyclic, organic peroxyacids are known and used, among others, in the detergent field.

Already-described peroxycarboxylic acids are, e.g., di-peroxydodecanedioic acid, monoperoxyphthalic acid, diperazelaic acid, substituted diperoxyglutaric and adipic acids, etc,..

In particular, formulations based on persalts and/or amide-derivative peracids, which operate also at low temperature, are known. These peroxyacids, however, are not within the class of the imide-aromatic peroxycarboxylic acids of the present invention.

One object of the present invention is, therefore, to provide a particular class of imide-aromatic poly(peroxyacids) particularly efficacious as bleaching agents in the washing of textile materials.

Another object is to provide bleaching agents which operate at low temperature, without damaging the fibers and/or the color of the fabrics.

These and still other objects of the invention will become even clearer to those skilled in the art from the following description of bleaching agents constituted by at least one imide-aromatic (poly)peroxyacid having the formula (I):

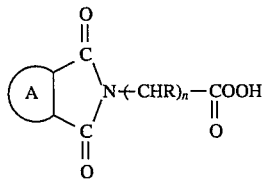

wherein A represents a residue of a substituted or unsubstituted benzene or naphthalene ring, the symbol or symbols R, which may be equal to or different from each other, represent a hydrogen atom or an optionally substituted $C_1$–$C_5$ alkyl group, an OH group, a COOH group, a COOOH group or a COOR' group, wherein R' represents a $C_1$–$C_5$ alkyl group, and n is an integer from 1 to 5.

The $C_1$–$C_5$ alkyl R groups may in turn be substituted with $C_1$–$C_5$ alkoxy groups, hydroxyl groups, nitro groups and so forth; the residue A by a COOH group, etc.

The following imide-aromatic (poly)peroxyacids having formula (I) have proved to be particularly efficacious: phthalimide-peracetic acid, 3-phthalimide-perpropionic acid, 4-phthalimide-perbutyric acid, 2-phthalimide-di-perglutaric acid, 2-phthalimide-di-persuccinic acid, 3-phthalimide-perbutyric acid, 2-phthalimide-per-propionic acid, methyl semi-ester of 2-phthalimide-mono-per-glutaric acid, 3-phthalimide-di-peradipic acid, naphthalimide-peracetic acid, 2-phthalimide-mono-persuccinic acid and 4-(4-percarboxy)phthalimide-peroxybutyric acid.

They are obtained according to substantially conventional methods. For example, by the reaction of a substrate consisting essentially of the imide-aromatic (poly)carboxylic acid (having the structure corresponding to the desired peracid having formula (I)) with $H_2O_2$ in sulphuric or methanesulphonic acid, and by subsequent separation and so forth according to known techniques, or by operating in an alkaline medium, according to known methods, starting from the corresponding anhydrides.

In fact, when at least one -(CHR)- residue, present in the formula of the starting substrate, contains a carboxylic group, it is possible to prepare the corresponding peracids having the above defined formula (I) by using the relevant anhydrides.

In this case, depending on the operating conditions (acid or alkaline medium and so forth), di- or monoperoxyacids may be selectively obtained, namely peroxyacids containing two peroxycarboxylic groups or a peroxycarboxylic group and a carboxylic group.

According to a preferred operating mode, the peroxycarboxylation reaction of the acid or poly-acid used as the starting substrate is carried out by gradually adding $H_2O_2$, having a concentration within the range of from approximately 70% to approximately 90% by weight, to a solution of the substrate in concentrated $H_2SO_4$, or in $CH_3SO_3H$, by maintaining the reaction temperature throughout the reaction within the range of from approximately 15° to approximately 50° C., depending on the reactivity of the substrate.

The amount of $H_2SO_4$ or of $CH_3SO_3H$, calculated at a concentration of 100%, is from 3 to 20 moles per mole of substrate, and is preferably from approximately 4 to 14 moles per mole of substrate.

The hydrogen peroxide is used in an amount which is in excess with respect to the substrate, and is from approximately 2 to 6 moles per mole of substrate, and preferably from approximately 2.2 to 5 moles per mole of substrate, depending on the COOH groups to be percarboxylated.

The reaction time depends on the nature of the substrate, on the operating temperature, and on the end total $H_2SO_4$/$H_2O$ or $CH_3SO_3H$/$H_2O$ molar ratio present at the end of the reaction. Said ratio is from approximately 1 to 6; and preferably from approximately 1.6 to 4, by changing the various parameters.

Reaction times from approximately 30 minutes to 2 hours have been shown to be operative.

The separation of the imide-aromatic (poly)peroxyacid having formula (I) is carried out according to conventional techniques such as by the filtration of the solid precipitate obtained after treatment of the reaction mixture with an ammonium sulfate solution, or by extraction with solvents and so forth.

The imide-aromatic (poly)peroxyacids having the above defined formula (I) are thus obtained in the form of crystalline solids.

The substrates used as the starting materials are per se known compounds, or may be prepared according to conventional techniques. Suitable substrates are for exemplary purposes: phthalimide-acetic acid, 3-phthalimide-propionic acid, 4-phthalimide-butyric acid, 2-phthalimide-glutaric acid and the corresponding anhydride, 2-phthalimide-succinic acid and the corresponding anhydride, 3-phthalimide-burytic acid, 2-phthalimide-propionic acid, methyl semiester of 2-phthalimide-glutaric acid, 3-phthalimide-adipic acid, naphthalimide-acetic acid, phthaloyl serine, 4-(4-carboxy)- phthalimide-butyric acid, and so forth, from which the above preferred peracids of formula (I) are obtained.

The peroxycarboxylic acid products having formula (I) are usually solid at room temperature.

According to the present invention, they may be used in detergent formulations, e.g., granular formulations, as bleaching agents in solution for use over a wide temperature range, e.g., between approximately 20° and 90° C.

Therefore, the imide-aromatic peroxyacids of the present invention may be used as bleaching agents directly alone, e.g., separately from the detergent composition, or, preferably, associated with and incorporated into conventional detergent compositions, which operate within the above defined temperature range, and containing other components and/or additives such as, e.g., builders, surfactants, soaps, zeolites, hydrotropic agents, corrosion inhibitors, enzymes, optical brighteners, stabilizers, other brightener compounds, and so forth.

Preferably, the operating temperature is between room temperature and approximately 65° C.

The preparation and uses of the compositions as well as their formulations are comprised in the described and/or conventional fields of use.

The imide-aromatic peroxyacids of the present invention may be used in combination with solid and liquid detergent compositions and/or in the presence of other bleaching peroxy compounds.

Further, the imide-aromatic peroxyacids may be subjected to a phlegmatization process according to known art.

EXAMPLES

The present invention will now be disclosed in still further detail in the following examples, which are supplied for purely illustrative and not limiting purposes.

The products prepared in the examples were characterized by elemental analysis, by determining their content of active oxygen (by iodometric titration), and by using Fourier Transform Infrared Spectroscopy (FT-IR).

In the examples, the term "EO" means ethylene oxide; the percentages are expressed by weight. "DIXAN" and "BIO PRESTO" are commercial Trademarks of detergents available on the market and produced by HENKEL - ITALY and LEVER - ITALY, respectively.

Example 1

330 g (3.434 moles) of methanesulphonic acid were charged into a beaker equipped with stirrer, thermometer and outer bath.

The internal temperature was increased to 25° C., and 55 g (0.268 mole) of phthalimide-acetic acid were added under stirring for 15 minutes.

The temperature was then lowered to 10° C. whereupon 44 g of $H_2O_2$ at 70% (0,906 mole) were gradually added, under stirring, so that the temperature was maintained lower than 15° C.

The stirring was continued at 15° C. for 1.5 hours.

At the end of this time, the reaction mixture was poured into 600 ml of $(NH_4)_2SO_4$ at 20% maintained under stirring at 5° C.

The stirring was continued for 15 minutes at a temperature between 5° and 10° C.

The solid product was filtered under vacuum over a porous septum. Thus, the obtained product was suspended in 400 ml of $Na_2SO_4$ at 8% and neutralized at pH 6 by $Na_2CO_3$ at 15%.

The resulting solid was then again filtered, washed with (100 ml) ice water, wiped and dryed on a porous plate inside a $CaCl_2$-drier under vacuum (2 mm Hg) at room temperature.

58 g of substantially pure phthalimide-peracetic acid were obtained. Yield: 97%.

The product may be recrystallized by dissolving it directly in ethyl acetate and by adding petroleum ether up to solution turbidity.

Elemental Analysis:

Computed for $C_{10}H_7O_5N$: C: 54.30%; H: 3.19%; N: 6.33%; O (active): 7.23%.

Found; C: 54.32%; H: 3.33%; N: 6.57%; O (active): 7.2%.

Melting Point: 118° C. (with decomposition).

Example 2

28 g (0.274 mole) of $H_2SO_4$ at 96% were charged into a beaker equipped with stirrer, thermometer and outer bath.

The inner temperature was brought to 25° C. and 11.7 g (0.0534 mole) of 3-phthalimide-propionic acid were added under stirring for 15 minutes.

The temperature was lowered to 10° C. and 5.2 g of $H_2O_2$ at 70% (0.107 mole) were gradually added under stirring so that the temperature was maintained lower than 15° C.

The stirring was continued at 15° C. for 1.5 hours. At the end of this time, the reaction mixture was then poured into 80 ml of (NH4)2SO$_4$ at 20% maintained under stirring at 5° C. The stirring was continued for 15 minutes at a temperature between 5° and 10° C.

The solid product was filtered under vacuum over a porous septum.

The obtained product was suspended in 50 ml of $Na_4SO_4$, at 8% and neutralized at pH 6 with $Na_2CO_3$ at 15%. The resulting solid was again filtered, washed with 20 ml of ice water, wiped and dried on a porous plate into a $CaCl_2$-drier under vacuum (2 Hg mm) at room temperature.

11.3 g of substantially pure 3-phthalimide-perpropionic acid were obtained. Yield: 90%.

The product may be recrystallized as described in Example 1.

Elemental Analysis

Computed for $C_{11}H_9O_5N$; C: 56.17%; H: 3.85%; N: 5.95%; O (active) 6.80%.

Found: C: 56.83%; H: 4.01%; N: 6.10%; O (active): 6.79%.

Melting point: 91° C. (with decomposition).

Example 3

The procedures of Example 2 were repeated by replacing the 3-phthalimide-propionic acid with 4-phthalimide burytic acid (15 g; 0.0643 mole), and by using 30 g of $H_2SO_4$ at 96% (0.294 mole), 7 g of $H_2O_2$ at 70% (0.144 mole), and by prolonging the reaction time to 2 hours.

14.5 g of substantially pure 4-phthalimide-perbutyric acid were obtained. Yield: 90%.

The product may be recrystallized as described in Example 1.
Elemental Analysis

Computed for $C_{12}H_{11}O_5N$; C: 57.83%; H: 4.45%; N: 5.62%; O (active): 6.42%.

Found: C: 57.98%; H: 4.52%; N: 5.69%; O (active): 6.41%.

Melting Point: 103° C. (with decomposition).

Example 4

The procedures of Example 1 were repeated by replacing phthalimide-acetic acid with 2-phthalimide-glutaric acid (6 g; 0.0216 mole), and by using 28 g (0.291 mole) of methanesulphonic acid and 3.5 g of $H_2O_2$ at 85% (0.0875 mole).

At the end 15 ml of $(NH_4)_2SO_4$ at 40% were gradually added to the reaction mixture, cooled at 0° C., so that the temperature was maintained from 0° to 5° C.

The resulting mixture was extracted with $Et_2O$ (6×30 ml).

The ether extract was washed with 30 ml of $(NH_4)_2SO_4$ at 40%, dried on anhydrous $Na_2SO_4$, filtered and evaporated.

An oil was obtained which was dissolved in $Et_2O$ (20 ml) and precipitated in the solid state by petroleum ether (40 ml), by maintaining the mixture under agitation up to complete solidification.

After filtration, 5.8 g of 2-phthalimide-diperglutaric acid at 95% were obtained. Yield: 82%.

The product was recrystallized as described in Example 1.
Elemental Analysis

Computed for $C_{13}H_{11}O_8N$; C: 50.49%; H: 3.58%; N: 4.53%; O (active): 10.34%.

Found: C: 49.96%; H: 3.75%; N: 4.70%; O (active): 10.33%.

Melting Point: 112° C. (with decomposition).

Example 5

The procedures of Example 4 were repeated by replacing 2-phthalimide-glutaric acid with 2-phthalimide-succinic acid (5 g; 0.019 mole), by using 20 g (0.208 mole) of methanesulphonic acid, 3.8 g (0.095 mole) of $H_2O_2$ at 85%, and by extending the reaction time to 2 hours.

At the end, 80 ml $(NH_4)_2SO_4$ at 40% were gradually added to the reaction mixture cooled at 0° C., so that the temperature was maintained at between 0° and 5° C.

The stirring was continued for 15 minutes, always at 0° to 5° C.

The procedures of Example 2 were then followed.

4 g of substantially pure 2-phthalimide-dipersuccinic acid were obtained. Yield: 71%.

The product may be recrystallized as described in Example 1.
Elemental Analysis

Computed for $C_{12}H_9O_8N$; C: 48.82%; H: 3.07%; N: 4.74%; O (active): 10.84%.

Found: C: 48.44%; H: 3.22%; N: 4.88%; O (active): 10.82%.

Melting Point: 131° C. (with decomposition).

Example 6

The procedures of Example 5 were repeated, by replacing 2-phthalimide-succinic acid with 2-phthalimide-succinic anhydride (2 g; 0.0082 mole), and by using 10 g (0.104 mole) of methanesulphonic acid and 1.3 g (0.0325 mole) of $H_2O_2$ at 85%, and by reducing the reaction time to 1.5 hours.

At the end, 60 ml of $(NH_4)_2SO_4$ at 20% were gradually added to the reaction mixture, cooled to 0° C., so that the temperature was maintained at between 0° and 5° C.

The resulting mixture was extracted with $EtOAc/Et_2O$ 1:2 (2×30 ml). The organic extract was washed with 20 ml of $(NH4)_2SO_4$ at 20%, dried on anhydrous $Na_2SO_4$, filtered and evaporated under vacuum.

1.8 g of 2-phthalimide-dipersuccinic acid were obtained at 95%.

Found: O (active): 10.3%; O (active) computed for $C_{12}H_9O_8N$: 10.84%.

Example 7

5 g of a $Na_2CO_3$ solution at 17.4% were charged into a 50 ml beaker. The inner temperature was brought to 5° C. and 0.8 g of $H_2O_2$ at 85% and 0.04 g of $MgSO_4 \cdot 7 H_2O$ were charged.

Maintaining the temperature at 5° C., 2 g of 2-phthalimide-succinic anhydride (0.0082 mole) were subsequently charged.

The inner temperature was left to gradually increase to 20° C., by continuing the stirring for 30 minutes.

30 ml of ethyl ether and 4.2 g of $H_2SO_4$ at 20% were then added. The ether layer was successively separated and washed with $(NH_4)_2SO_4$ at 40% (2×20 ml); it was dried on anhydrous $Na_2SO_4$ and then, after the filtration of the sulphate, the peracid was precipitated with 30 ml of petroleum ether, by stirring the mixture at room temperature for 30 minutes. The peracid was filtered and again dried under vacuum at room temperature.

1.5 g of product at 63% as 2-phthalimide-mono-persuccinic acid were obtained.

Found O (active): 3.6% O (active), computed for $C_{12}H_9NO_7$: 5.73%.

Example 8

1.5 g of $H_2O_2$ at 85% (0.0375 mole) was added to 2 g of 4-(4-carboxy)-phthalimide burytic acid (0.0072 mole) in 12 g of methanesulphonic acid (0.125 mole) suspension, under stirring at 15° to 20° C. Stirring was continued for 2 hours at 15° C.

The reaction product was then poured into 40 ml of $(NH_4)_2SO_4$ at 40, maintained at 5° C. and, after 15 minutes stirring, the separated solid product was filtered. This latter was then neutralized at pH 6, by suspending it in an 8% $Na_2SO_4$ solution and by adding $Na_2CO_3$ at 15%.

The resulting solid was again filtered, washed with ice water (30 ml), and dried over a porous plate in a $CaCl_2$-drier.

The product may be recrystallized by dissolving it in ethyl acetate at room temperature and again precipitating by adding petroleum ether.

There were thus obtained 2 g of substantially pure 4-(4-percarboxy)-phthalimide peroxybutyric acid. Yield 90%.
Elemental Analysis Computed for $C_{13}H_{11}O_8N$; C: 50.49%; H: 3.58%; N: 4.53%; O (active): 10.35%.

Found: C: 50.04%; H: 3.75%; N: 4.48%; O (active): 10.34%.

Melting point: 109° C. (with decomposition).

Example 9 (Application Example)

(Bleaching with phthalimide-peracetic acid (FIPA))

Bleaching tests were carried out with a detergent formulation containing FIPA (composition D) in the amount reported in the following Table 1, in comparison with similar compositions containing, as bleaching agents, tetrahydrated sodium perborate (PBS) (composition A), PBS activated with TAED (tetra-acetyl-ethylene-diamine) in the stoichiometric ratio (composition B), and the H 48 peracid (Mg salt of the mono-perphthalic acid), a peracid known on the market, produced by INTEROX Chemical Ltd., London, Great Britain, for the detergency (composition C). In order to complete the test, two among the best detersives known on the Italian market: "BIO PRESTO" (composition E) and "DIXAN" (composition F) were further included for comparison sake.

The first composition containing TAED as activator and, therefore, was suitable for the washing at low temperature and the second one without activator, but with a high content of PBS and, therefore, suitable for the washing at high temperature.

The non-commercial formulations were prepared by dry blending of a detergent base, common to all the above formulations, and hereinafter more fully defined, with the listed bleaching products. As a detergent base, a granular composition was used containing all the normal conventional components of a detergent for a washing machine (surfactants, builders, etc.), except the chemical bleaching agents, and obtained by atomization of the mixture of the same components.

The detergent base used had the following composition;

|  | Weight % |
|---|---|
| Total surfactants | 15.4 |
| (Sodium alkyl ($C_{12}$) benzene-sulphonate, soap, alcohol ($C_{16}$–$C_{18}$) ethoxylate 7 EO) | |
| Total sodium phosphates | 8.8 |
| Zeolite A | 19.8 |
| Silicate ($SiO_2/Na_2O = 2$) | 4.4 |
| Sodium sulphate | 36.6 |
| Sodium carbonate | 6.6 |
| Carboxymethylcellulose | 1.1 |
| Anti-encrusting co-polymers | 4.8 |
| Water | 2.2 |
| Optical bleaching agents | 0.3 |

The amounts of the tested bleaching agents were determined so that each formulation has the same content of active oxygen (1.4%) by adding, where necessary, sodium sulphate to complete the composition.

Correspondingly, the commercial detersives used on a comparative basis had the following composition:

|  | BIO PRESTO Weight % | DIXAN Weight % |
|---|---|---|
| Total surfactants | 13.8 | 12.7 |
| (Straight alkyl ($C_{12}$) benzene-sulphonate, soap, alcohol ($C_{16}$–$C_{18}$) ethoxylate 7 EO) | | |
| Total sodium phosphates | 6.6 | 8.0 |
| Zeolite A | 18.4 | 16.6 |
| Sodium silicate ($SiO_2/Na_2O = 2$) | 3.9 | 2.8 |
| Mono-hydrate sodium perborate | 8.3 | — |
| Tetrahydrate sodium perborate | — | 27.6 |
| Sodium sulphate | 33.2 | 22.0 |
| Sodium carbonate | 6.2 | 10.6 |
| Carboxymethylcellulose | 1.0 | 1.0 |
| Anti-encrusting co-polymers | 4.5 | 3.5 |
| Tetra-acetyl-ethylene-diamine (activator) | 1.8 | — |
| Water | 1.9 | 0.4 |
| Optical bleaching agents, enzymes, perfume and others | to 100 | to 100 |

The experimental formulations (A–F) had the compositions summarized in the following Table 1.

TABLE 1

| Composition A | |
|---|---|
| Detergent base | 80% |
| PBS at 10% of active oxygen | 14% |
| $Na_2SO_4$ | 6% |
| Composition B | |
| Detergent base | 75% |
| PBS at 10% of active oxygen | 14% |
| TAED at 95% of active substance | 11% |
| Composition C | |
| Detergent base | 74% |
| H.48 at 5.5% of active oxygen | 26% |
| Composition D | |
| Detergent base | 80% |
| FIPA at 7.1% of active oxygen | 20% |
| Composition E | |
| "BIO PRESTO" commercial detersive for washing machines of the LEVER firm containing 13% of PBS (in the form of tetrahydrate ) + about 2% of TAED | |
| Composition F | |
| "DIXAN" commercial detersive for washing machines of the HENKEL firm containing approximately 28% of tetrahydrate PBS. | |

The tests were carried out in an IGNIS MOD. 644 commercial washing machine by introducing into the machine two cotton specimens 15×15 cm stained in the standard way with red wine at EMPA INSTITUTE of St. Gallen (Switzerland) and marked with the "EMPA 114" mark, together with 3 Kg clean cotton dusters, as ballast, for each washing cycle.

The dosage was 150 g in each washing cycle for each formulation.

The washings were carried out by standard programs at medium temperature (approximately 60° C.) and at low temperature (approximately 40° C.). A program at high temperature (85°–90° C.) was used only for DIXAN; this was in order to develop the maximum level of bleaching which may be really obtained. Normal undistilled tap water, having a hardness of 14° was used.

The results of the tests are reported in the following Table 2, wherein the data are expressed as bleaching percent wherein:

$$\text{Bleaching \%} = \frac{A-B}{C-B} \times 100$$

wherein:
A=degree of whiteness (%) of the specimen bleached during the test;
B=degree of whiteness (%) of the specimen before the test;
C=degree of whiteness (%) of the completely bleached specimen, and
wherein the degrees of whiteness were measured by means of an Elrepho Zeiss Reflectometer by using a filter N. 6 ($\lambda$=464 mm) and by assuming MgO=100% of whiteness.

TABLE 2

| | Bleaching % | | |
|---|---|---|---|
| | Washing Program | | |
| | At low temperature (40° C.) | At medium temperature (60° C.) | At high temperature (85°–90° C.) |
| Composition A | 33.3 | 43.7 | — |
| Composition B | 51.4 | 74.8 | — |
| Composition C | 63 | 76 | — |
| Composition D | 79.4 | 89.9 | — |
| Composition E | 32.8 | 66.1 | — |
| Composition F | — | — | 92.5 |

The data show that:
the FIPA bleaching powder exceeds that of all the other tested bleaching formulations; at medium temperature it allows one to obtain bleaching results very close to the maximum, which may be obtained only at high temperature and by using high amounts of active oxygen (DIXAN);
excellent results, and significantly higher than the other formulations, may be obtained even more surprisingly by FIPA at low temperature;
the activated PBS is less effective than the peracids at low temperature even if the activation is complete
(see B v. C and D).
The modest content of activator in the commercial detersive (E), due mostly to storage stability problems, has as a consequence that the bleaching result at low temperature cannot be differentiated from that of non-activated PBS (A) and that this result at medium temperature is very far from that which may be potentially obtained by activator (B).

Examples 10–13 (Application Examples)

Bleaching tests were carried out in the same concentration of active oxygen in the bleaching solution, and by using the imide-aromatic peroxyacid, as in the present invention, shown in the following Table I, as compared to H.48 product.

The procedure was as follows: All tests were carried out at the constant temperature of 60° C., with an initial concentration of total active oxygen in the bleaching equal for all products, and equal to 200 mg/l.
Process
For each test, 500 ml of deionized water, contained in a 1,000 ml flask equipped with a condenser, was heated to a temperature of 60° C. and adjusted to a pH value of 9.5 (with a few drops of an NaOH solution); then the bleaching product was added, under stirring, in the amounts as reported in the following Table 3, and immediately thereafter, two cotton specimens of 10×10 cm stained in the standard way by red wine at EMPA INSTITUTE of St. Gallen (Switzerland), and marked with the "EMPA 114" mark, were added.

The system was subsequently kept under stirring for 60 minutes and, at the end of this time, the specimens, rinsed under running water, were dried and, ironed, and were then submitted to evaluation of the bleaching effect by means of measurements of whiteness degree by reflectometry. The results are reported in the following Table 3, wherein the data are expressed as Bleaching %, as defined in the above Example 8.

The data in Table 3 show that the peracids of the present invention have a bleaching power in an amount which may be compared with that of H.48 and in some cases also higher than it.

TABLE 3

| Compound | Amounts used in the test (grams) | Initial concentration of total active oxygen (mg/l) | Bleaching % |
|---|---|---|---|
| Example 1 (titer: 7.2% active oxygen) | 1.46 | 200 | 83.6 |
| Example 2 (titer: 6.79% of active oxygen) | 1.47 | 200 | 83.0 |
| Example 3 (titer: 6.41% of active oxygen) | 1.56 | 200 | 79.4 |
| Example 4 (titer: 9.81% of active oxygen) | 1.02 | 200 | 74.0 |
| Example 5 (titer 10.82% of active oxygen) | 0.924 | 200 | 75.0 |
| H.48 (titer: 5.5% of active oxygen) | 1.86 | 200 | 75.1 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The references are hereby incorporated by reference.

What is claimed is:
1. In a bleaching composition comprising a detergent and a bleaching agent, the improvement wherein the bleaching agent is capable of being effectively operated at a temperature between 20° and 90° C., and is an imide-aromatic (poly)peroxycarboxylic acid having the formula

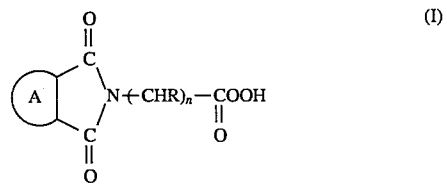

wherein A represents the residue of a benzene or naphthalene ring optionally substituted by a COOH or COOOH group; the symbol or symbols R, which may be equal to or different from each other, represent a hydrogen atom, a $C_1$–$C_5$ alkyl group, an OH group, a COOH group, a COOOH group, a COOR' group wherein R' represents a $C_1$–$C_5$ alkyl group, or a substituted $C_1$–$C_5$ alkyl group wherein the substituent is nitro, an OH group, or a $C_1$–$C_5$ alkoxy group, and n is an integer from 1 to 5.

2. The composition of claim 1 wherein A is substituted with a COOH group.

3. The bleaching composition of claim 1, wherein the bleaching agent is selected from the group consisting of phthalimide-peracetic acid, 3-phthalimide perpropionic acid, 4-phthalimide-perbutyric acid, 2-phthalimide-diperglutaric acid, 2-phthalimide-dipersuccinic acid, 3-phthalimide-perbutyric acid, 2-phthalimide-perpropionic acid, 3-phthalimide-diperadipic acid, and naphthalimide-peracetic acid.

4. In a solid or liquid formulation comprising a detergent, a bleaching agent, and other components or additives selected from the group consisting of builders, surfactants, soaps, zeolites, hydrotropic agents, corrosion inhibitors, enzymes, optical bleaching agents, stabilizers, and mixtures thereof, the improvement wherein said bleaching agent is as defined in claim 1.

5. The bleaching composition of claim 1 wherein said bleaching agent comprises omega-phthalimido peroxyhexanoic acid.

* * * * *